(12) United States Patent
Park et al.

(10) Patent No.: US 11,771,345 B2
(45) Date of Patent: Oct. 3, 2023

(54) FOOTPRINT GENERATOR CAPABLE OF APPLYING CONSTANT FORCE AND FOOTPRINT GENERATION METHOD USING THE SAME

(71) Applicant: REPUBLIC OF KOREA (NATIONAL FORENSIC SERVICE DIRECTOR MINISTRY OF THE INTERIOR AND SAFETY), Wonju-si (KR)

(72) Inventors: Nam Kyu Park, Bucheon-si (KR); Byung Seon Moon, Busan (KR); Jae Mo Goh, Wonju-si (KR); Jin Pyo Kim, Daejeon (KR); Young Il Seo, Wonju-si (KR); Eun Ah Joo, Yongin-si (KR); Je Hyun Lee, Wonju-si (KR); Sang Yoon Lee, Wonju-si (KR)

(73) Assignee: REPUBLIC OF KOREA (NATIONAL FORENSIC SERVICE DIRECTOR MINISTRY OF THE INTERIOR AND SAFETY), Wonju-si (KR)

( * ) Notice: Subject to any disclaimer, the term of this patent is extended or adjusted under 35 U.S.C. 154(b) by 203 days.

(21) Appl. No.: 17/362,421

(22) Filed: Jun. 29, 2021

(65) Prior Publication Data
US 2022/0354388 A1    Nov. 10, 2022

(30) Foreign Application Priority Data

May 6, 2021    (KR) .................... 10-2021-0058619

(51) Int. Cl.
*G01N 3/08*    (2006.01)
*G01N 3/42*    (2006.01)
(Continued)

(52) U.S. Cl.
CPC .............. *A61B 5/1174* (2013.01); *G01N 3/08* (2013.01); *G01N 2203/0003* (2013.01); *G01N 2203/0026* (2013.01); *G01N 2203/0208* (2013.01)

(58) Field of Classification Search
CPC ... G01N 2203/0208; G01N 2203/0026; G01N 2203/0003; G01N 3/08; A61B 5/1174;
(Continued)

(56) References Cited

U.S. PATENT DOCUMENTS

| 6,854,316 B2 * | 2/2005 | Hage ...................... G01N 19/02 73/9 |
| 6,988,416 B1 * | 1/2006 | Norton ..................... G01N 3/08 73/818 |
| 2012/0297889 A1 * | 11/2012 | Yngve ................... G01N 19/02 73/818 |

FOREIGN PATENT DOCUMENTS

| CN | 1717580 A * | 1/2006 | ............. G01N 19/02 |
| JP | 2017-131614 A | 8/2017 | |

(Continued)

OTHER PUBLICATIONS

Korean Office dated May 3, 2022, in connection with the Korean Patent Application No. 10-2021-0058619.

*Primary Examiner* — Brandi N Hopkins
(74) *Attorney, Agent, or Firm* — Hauptman Ham, LLP

(57) ABSTRACT

A footprint generator capable of applying a constant force includes: a base plate in which a target surface may be on an upper surface of the base plate; a shoe mounting member that is apart from the upper surface of the base plate and capable of mounting a shoe; a driving unit that is apart from the upper surface of the base plate and capable of moving the shoe mounting member up and down; and a force measuring unit configured to measure an impact force when the shoe
(Continued)

mounting member descends and contacts the shoe with the target surface to generate a footprint on the target surface.

6 Claims, 6 Drawing Sheets

(51) Int. Cl.
    *G01N 3/48*           (2006.01)
    *G01L 5/00*           (2006.01)
    *A61B 5/1174*        (2016.01)

(58) Field of Classification Search
    CPC ..... A61B 5/1038; A61B 5/1036; G06F 3/016;
        A43B 3/38; A43B 13/18; A63B 21/0053;
        A63B 24/0087; A61G 5/061; A61H 3/00;
                                G01B 21/00
    See application file for complete search history.

(56) References Cited

FOREIGN PATENT DOCUMENTS

| | | |
|---|---|---|
| KR | 10-1251452 B1 | 4/2013 |
| KR | 10-1367724 B1 | 2/2014 |
| KR | 10-2019-0102879 A | 9/2019 |

\* cited by examiner

FOOTPRINT GENERATOR CAPABLE OF APPLYING CONSTANT FORCE AND FOOTPRINT GENERATION METHOD USING THE SAME

CROSS-REFERENCE TO RELATED APPLICATION

This application claims the benefit of Korean Patent Application No. 10-2021-0058619, filed on May 6, 2021, in the Korean Intellectual Property Office, the disclosure of which is incorporated herein in its entirety by reference.

BACKGROUND

1. Field

One or more embodiments relate to a footprint generator capable of applying a constant force and a footprint generation method using the same.

2. Description of the Related Art

Footprints include not only pedestrian traces left by criminals at the crime scene, but also wheel marks of vehicles and traces raised by various tools.

Footprints found at crime scenes are an important field of evidence that may contribute to solving the case through identity judgment and analysis when the suspect's shoes are presented, as well as estimating the size of the shoes and reconstructing the criminal's movement.

When the suspect's shoes are presented, it is determined whether they are identical to the footprints of the crime scene, and it is necessary to apply different levels of force when determining whether they are identical.

In addition, it is necessary to apply a constant force when generating footprints to control variables of a footprint experiment.

SUMMARY

One or more embodiments include a footprint generator capable of applying a constant force and a footprint generation method using the same.

In more detail, one or more embodiments include a footprint generator capable of generating footprints by applying various levels of force to the suspect's shoes when determining whether they are identical with the footprints at the crime scene, or applying a constant force to control variables during a footprint experiment, and a footprint generation method using the footprint generator.

According to one or more embodiments, a footprint generator capable of applying a constant force includes: a base plate in which a target surface may be on an upper surface of the base plate; a shoe mounting member that is apart from the upper surface of the base plate and capable of mounting a shoe; a driving unit that is apart from the upper surface of the base plate and capable of moving the shoe mounting member up and down; and a force measuring unit configured to measure an impact force when the shoe mounting member descends and contacts the shoe with the target surface to generate a footprint on the target surface.

In an embodiment, the driving unit may be formed in a shape rotatable about a horizontal axis, and may be capable of rotating the shoe mounting member at a certain angle or more about the horizontal axis of the driving unit.

In an embodiment, the shoe mounting member may include a shoe fixing unit capable of fixing shoes; and a connecting unit formed to connect the driving unit to the shoe fixing unit to rotate the shoe fixing unit about the horizontal axis of the driving unit.

In an embodiment, the footprint generator capable of applying a constant force may further include an input unit configured to receive an input signal according to a user input; a control unit configured to operate the driving unit according to the user input to control the shoe mounting member on which the shoe is mounted to descend and generate a footprint on the target surface; and a display unit configured to display user input information capable of operating the driving unit with a constant force or operation information of the driving unit.

In an embodiment, the user input information may include the amount of force applied to the target surface, the number of times the driving unit is operated, or an angle at which the shoe mounting member rotates about the horizontal axis of the driving unit.

In an embodiment, the input unit, the control unit, and the display unit may be formed as a single control panel.

In an embodiment, the footprint generator capable of applying a constant force may further include a fixing unit capable of fixing the shoe mounting member and the driving unit in a position apart from the upper surface of the base plate.

According to one or more embodiments, a footprint generation method using a footprint generator capable of applying a constant force includes: mounting a shoe on a shoe mounting member of the footprint generator including a base plate, the shoe mounting member, a driving unit, and a force measuring unit; and generating a footprint on the target surface by lowering the shoe mounting member to contact the shoe with a target surface located on an upper surface of the base plate.

In an embodiment, the footprint generation method may further include: applying a colored solution to a sole of the shoe before the generating of the footprint on the target surface.

In an embodiment, the footprint generator may further include an input unit, a control unit, and a display unit, and the footprint generation method using the footprint generator capable of applying a constant force may further include obtaining user input information capable of operating the driving unit with a constant force after the mounting of a shoe on the shoe mounting member.

In an embodiment, the obtaining of user input information may include: measuring an impact force, by the force measuring unit, when a user inputs the descending speed of the driving unit and an angle at which the shoe mounting member rotates about a horizontal axis of the driving unit and generates a footprint on the target surface; and determining, by the user, the amount of force applied to the target surface, the number of times the driving unit is operated, or the angle at which the shoe mounting member rotates about the horizontal axis of the driving unit, based on the measured impact force.

In an embodiment, the generating of a footprint on the target surface may include: generating a plurality of footprints by applying a constant force by a user to the target surface or generating a footprint while changing the amount of force applied to the target surface at certain intervals, based on the obtained user input information.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
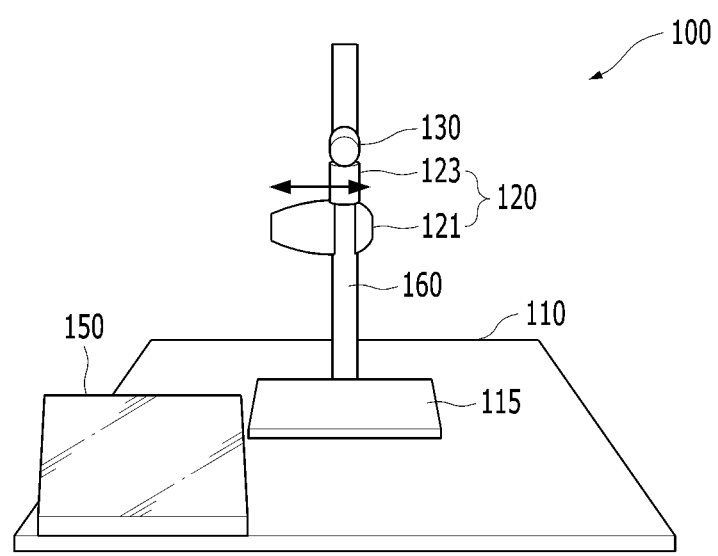
FIGS. 1 to 3 are exemplary views of a footprint generator capable of applying a constant force according to an embodiment.

Hereinafter, embodiments will be described in detail with reference to the accompanying drawings. The same reference numerals are used to denote the same elements, and repeated descriptions thereof will be omitted.

It will be understood that although the terms "first," "second," etc. may be used herein to describe various components, these components should not be limited by these terms.

An expression used in the singular encompasses the expression of the plural, unless it has a clearly different meaning in the context.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. That is, for example, intervening layers, regions, or components may be present.

Sizes of elements in the drawings may be exaggerated for convenience of explanation. In other words, since sizes and thicknesses of components in the drawings are arbitrarily illustrated for convenience of description, the following embodiments are not limited thereto. When a certain embodiment may be implemented differently, a specific process order may be performed differently from the described order. For example, two consecutively described processes may be performed substantially at the same time or performed in an order opposite to the described order.

It will be understood that when a layer, region, or component is connected to another portion, the layer, region, or component may be directly connected to the portion or an intervening layer, region, or component may exist. For example, when a layer, region, or component is electrically connected to another portion, the layer, region, or component may be directly electrically connected to the portion or may be indirectly electrically connected to the portion through another layer, region, or component.

Hereinafter, a footprint generator capable of applying a constant force according to an embodiment will be described with reference to FIGS. 1 to 4.

Figure 2:
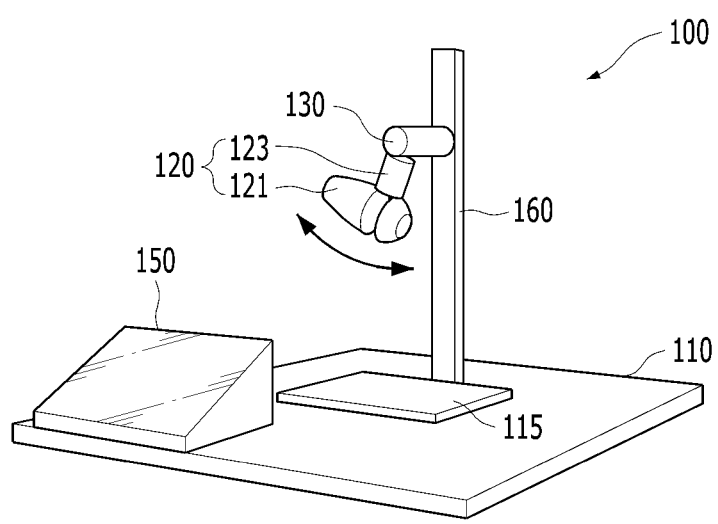
Figure 3:
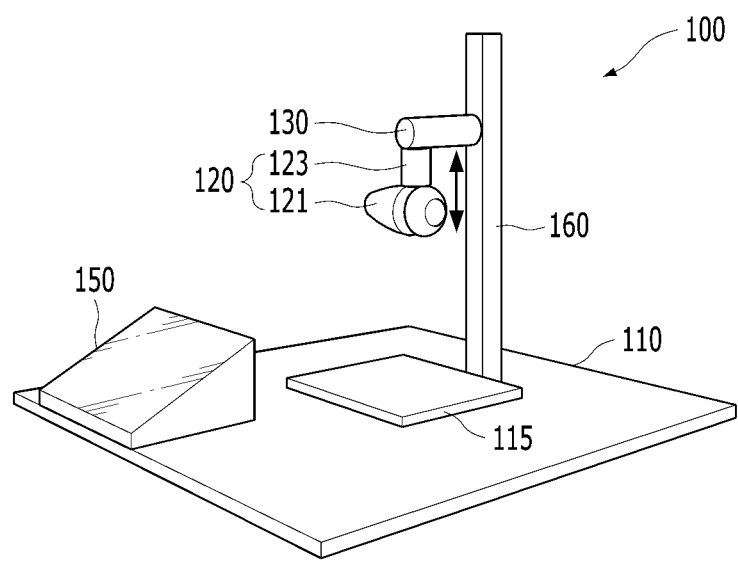
Figure 4:
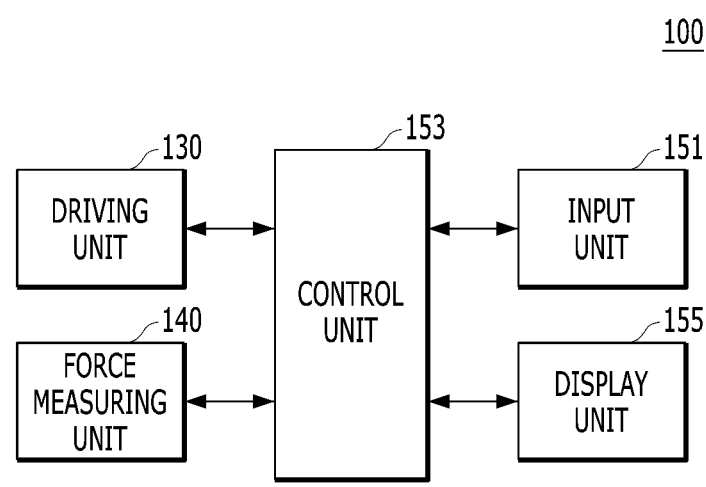
FIG. 4 is a block diagram of a footprint generator capable of applying a constant force according to an embodiment.

FIGS. 1 to 3 are exemplary views of a footprint generator capable of applying a constant force according to an embodiment, and FIG. 4 is a block diagram of a footprint generator capable of applying a constant force according to an embodiment.

Referring to FIGS. 1 to 4, a footprint generator 100 capable of applying a constant force according to an embodiment may include a base plate 110, a shoe mounting member 120, a driving unit 130, a force measuring unit 140, an input unit 151, a control unit 153, a display unit 155, and a fixing unit 160.

The base plate 110 may be on a horizontal bottom surface, and a target surface 115 may be on an upper surface of the base plate 110. Footprints may be generated on the target surface 115 by an impact, and details will be described later below. The target surface 115 may be formed of, for example, paper or floor paper.

Referring to FIGS. 1 and 3, the shoe mounting member 120 may be formed to mount a shoe (not shown), and may be connected to the driving unit 130 to move up and down. In this case, the shoe mounting member 120 may be apart from the upper surface of the base plate 110.

The shoe mounting member 120 may mount a shoe (not shown). The shoe mounting member 120 may include a shoe fixing unit 121 and a connecting unit 123.

The shoe fixing unit 121 may fix a shoe.

As an embodiment, the shoe fixing unit 121 may be formed in a shape in which one end is inserted into a front portion of a shoe and the other end is completely inserted into the rear portion of the shoe, like the shape of a human foot. In this case, the shoe fixing unit 121 may adjust the length according to the length of the shoe. Like wearing shoes on a person's foot, the shoe fixing unit 121 may be completely inserted into the shoe to fix the shoe.

As another embodiment, a shoe may be directly fixed to the shoe fixing unit 121 using an adhesive or the like.

A method for mounting a shoe on the shoe mounting member 120 is not limited to the above example. Any method may be used as long as the shoe comes into contact with the target surface 115 to form a footprint.

The connecting unit 123 may connect the driving unit 130 to the shoe fixing unit 121. The connecting unit 123 may be formed to rotate the shoe fixing unit 121 about a horizontal axis of the driving unit 130, and details will be described later below.

The driving unit 130 may move the shoe mounting member 120 up and down. The driving unit 130 is connected to the shoe mounting member 120 and may include a motor, a cylinder, or the like to change the position of the shoe mounting member 120 to move the shoe mounting member 120 up and down. By the driving unit 130, the shoe mounting member 120 on which a shoe is mounted descends from an initial position and rises immediately after contacting the target surface 115, thereby generating an instantaneous impact.

In addition, the driving unit 130 may be formed in a shape rotatable about the horizontal axis. For example, the driving unit 130 may be formed in a cylindrical shape or a bar shape located to be rotatable about the horizontal axis.

Accordingly, it is possible to rotate the shoe mounting member 120 at a certain angle or more about the horizontal axis of the driving unit 130. As such, the driving unit 130 may rotate the shoe mounting member 120 at a certain angle such that a sole of a shoe in contact with the target surface 115 forms an inclination of a certain angle with the target surface 115.

In addition, the driving unit 130 may be apart from the upper surface of the base plate 110. In this case, the driving unit 130 may be installed on the base plate 110 or fixed to the separate fixing unit 160 and installed.

The force measuring unit 140 may measure an impact force when the shoe mounting member 120 descends and makes a shoe contacts with the target surface 115 to generate a footprint on the target surface 115.

The shoe mounting member 120 on which a shoe is mounted descends from the initial position by the driving unit 130 and rises immediately after contacting the target surface 115 to generate an impact. At this time, a footprint is generated on the target surface 115 while the shoe is in contact with the target surface 115, and an impact force is generated. The force measuring unit 140 may measure the impact force at this time.

The force measuring unit 140 may be connected to the base plate 110 or the target surface 115, and is configured to measure the impact force received by the target surface 115 when the shoe mounting member 120 descends. For example, the force measuring unit 140 may be located at a point where the shoe mounted on the shoe mounting member 120 contacts the target surface 115.

For example, the force measuring unit 140 may include a load cell. The load cell is a sensor that converts a force into a measurable output signal. When a shoe and the target surface 115 are in contact with each other by an impact, the force measuring unit 140 detects an impact force and outputs the impact force as a signal to measure the amount of the impact force.

The input unit 151 is a unit for receiving an input signal for controlling or operating the footprint generator 100 capable of applying a constant force according to a user input, and may be implemented as various types of input units. For example, the input unit 151 may include a keyboard, a key pad, a touch pad, a jog wheel, a jog switch, and the like, but is not limited thereto.

The control unit 153 may generally control the operation of the footprint generator 100 capable of applying a constant force. The control unit 153 may be implemented in various forms such as a central processing unit (CPU), a processor, a microprocessor, an application processor (AP), a micro controller unit (MCU), a microcomputer, or a mini computer.

The control unit 153 may operate the driving unit 130 based on the user input of the input unit 151, and may control the shoe mounting member 120 on which a shoe is mounted to descend and generate a footprint on the target surface 115.

The display unit 155 may display all operating states of the footprint generator 100 capable of applying a constant force. In this case, the display unit 155 may display user input information capable of operating the driving unit 130 with a constant force or operation information of the driving unit 130. The user input information may include a force applied to the target surface 115, the number of times the driving unit 130 is operated, or an angle at which the shoe mounting member 120 rotates about the horizontal axis of the driving unit 130.

The footprint generator 100 capable of applying a constant force according to an embodiment may form the input unit 151, the control unit 153, and the display unit 155 into one control panel 150.

The control panel 150 may cause the control unit 153 to operate the driving unit 130 according to an input signal from the input unit 151 while performing a function of the input unit 151 receiving a user's touch input signal. In addition, the control panel 150 may simultaneously perform a function of the display unit 155 for displaying an operating state, including user input information for operating the driving unit 130 with a constant force or operation information of the driving unit 130.

In addition, the footprint generator 100 capable of applying a constant force according to an embodiment may further include the fixing unit 160.

The fixing unit 160 may fix the shoe mounting member 120 and the driving unit 130 in a position apart from the upper surface of the base plate 110. The fixing unit 160 may be directly connected to the base plate 110, or may not be directly connected to the base plate 110.

Figure 5:
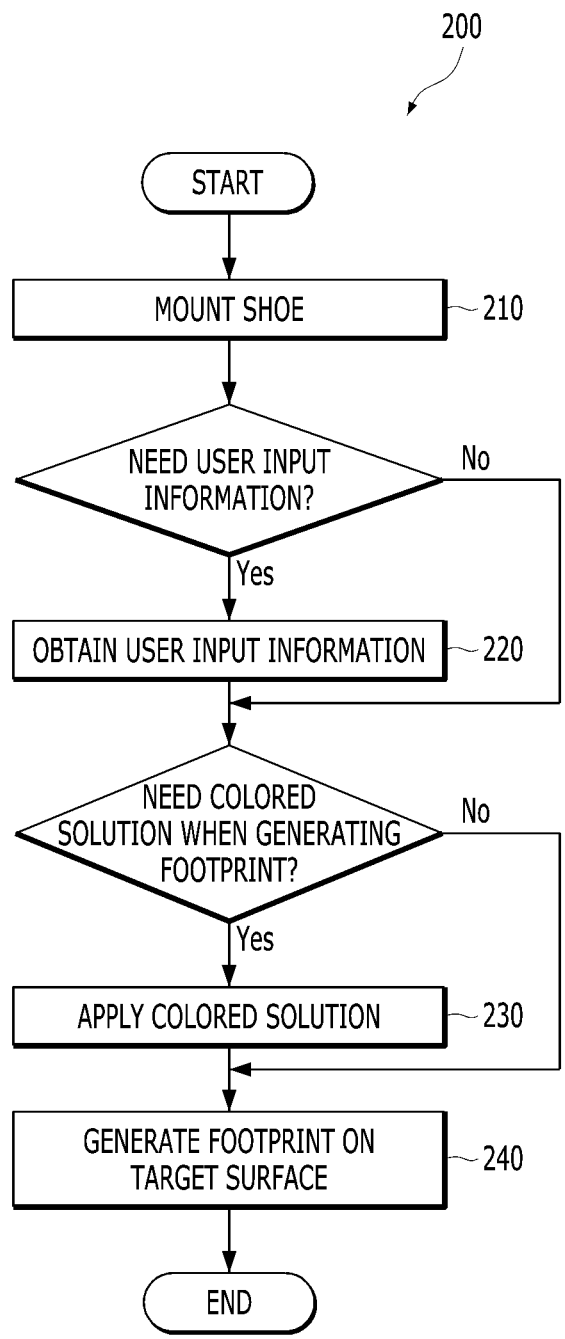
FIGS. 5 and 6 are flowcharts illustrating a footprint generation method using a footprint generator capable of applying a constant force according to an embodiment.
Figure 6:
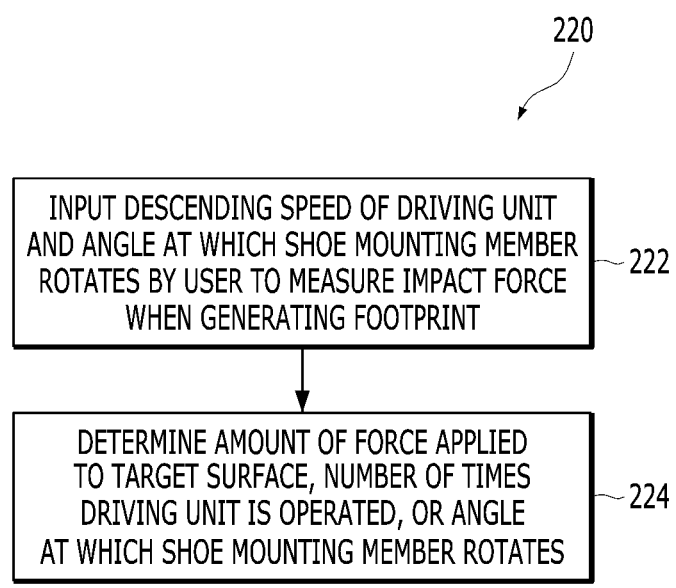

FIGS. 5 and 6 are flowcharts illustrating a footprint generation method using a footprint generator capable of applying a constant force according to an embodiment.

A footprint generation method 200 using a footprint generator capable of applying a constant force according to an embodiment will be described with reference to FIGS. 5 and 6.

The footprint generator 100 capable of applying a constant force according to an embodiment may include the base plate 110, the shoe mounting member 120, the driving unit 130, and the force measuring unit 140, and may further include the input unit 151, the control unit 153, and the display unit 155.

Operation 210 is mounting a shoe on the shoe mounting member 120 of the footprint generator 100 capable of applying a constant force according to an embodiment.

When it is not necessary to obtain user input information after operation 210, the following operations 230 and 240 may be performed. When it is necessary to obtain user input information after operation 210, operations 230 and 240 may be performed after operation 220 of obtaining user input information is performed.

Operation 220 is obtaining user input information. Operation 220 of obtaining user input information may include operations 222 and 224.

The user input information is information capable of operating the driving unit 130 with a constant force, and may include the amount of force applied to the target surface 115, the number of times the driving unit 130 is operated, or an angle at which the shoe mounting member 120 rotates about a horizontal axis of the driving unit 130.

In operation 222, the force measuring unit 140 may measure an impact force when a user inputs the descending speed of the driving unit 130 and the angle at which the shoe mounting member 120 rotates about the horizontal axis of the driving unit 130 and generates a footprint on the target surface 115.

The user may input the descending speed of the driving unit 130 to the input unit 151 while changing the descending speed, and according to the descending speed of the driving unit 130, a difference occurs in the impact force measured when footprints are generated on the target surface 115. In addition, the user may input the angle at which the shoe mounting member 120 rotates about the horizontal axis of the driving unit 130 to the input unit 151 while changing the angle at which the shoe mounting member 120 rotates about the horizontal axis of the driving unit 130, and accordingly, the impact force measured when footprints are generated and an inclination angle formed by a sole of a shoe with the target surface 115 may be changed. As such, there is a difference in the shape of a footprint according to the difference in the impact force measured when footprints are generated, and there is a difference in the shape of a footprint according to the difference in the rotation angle of the shoe mounting member 120.

Accordingly, the user may compare and determine shapes of footprints generated according to the change in the descending speed of the driving unit 130, in the impact force measured by the force measuring unit 140 when footprints are generated on the target surface 115, or in the angle at which the shoe mounting member 120 rotates about the horizontal axis of the driving unit 130.

In operation 224, the user determines the amount of force applied to the target surface 115, the number of times the driving unit 130 is operated, or the angle at which the shoe mounting member 120 rotates about the horizontal axis of the driving unit 130, based on the measured impact force.

The user may determine the range of the amount of force applied to the target surface 115 based on the measured impact force. At this time, the number of times the driving unit 130 is operated according to the amount of force applied to the target surface 115 may also be determined.

In addition, the user may determine the angle at which the shoe mounting member 120 rotates about the horizontal axis of the driving unit 130 based on the measured impact force. In this case, the number of times the driving unit 130 is operated according to the rotation angle of the shoe mounting member 120 may also be determined.

In operation 220, the user may find an operating condition of the driving unit 130 when a footprint is generated on the target surface 115. The user may comprehensively consider the shape of the footprint generated on the target surface 115 according to the various descending speeds of the driving unit 130 or the angle at which the shoe mounting member 120 rotates about the horizontal axis of the driving unit 130, and may determine the amount of force applied to the target surface 115, the number of times the driving unit 130 is operated, or the angle at which the shoe mounting member 120 rotates about the horizontal axis of the driving unit 130.

In operation 230, a colored solution (not shown) is applied to a sole of the shoe.

Various colored solutions, such as ink, blood, paint, etc., are applied to the sole of the shoe to generate a footprint on the target surface 115. However, in the case of generating a footprint only with dust attached to the shoe, the footprint may be generated without applying a colored solution, so that operation 230 may be omitted.

In operation 240, the shoe mounting member 120 descends to make the shoe contact with the target surface 115 on the upper surface of the base plate 110 to generate a footprint on the target surface 115.

At this time, based on the obtained user's input information, a user may generate a plurality of footprints by applying a constant force to the target surface 115. For example, a user may set the number of times the driving unit 130 is operated twice or more, fix the rotation angle of the shoe mounting member 120 at a constant level, and apply a constant force to generate a uniform footprint.

In addition, a user may generate a footprint while changing the amount of force applied to the target surface 115 at regular intervals. For example, while a user changes an angle at which the shoe mounting member 120 rotates about a horizontal axis of the driving unit 130, the amount of force applied by the user to the target surface 115 may be changed at regular intervals. However, the user may make the angle at which the shoe mounting member 120 rotates about the horizontal axis of the driving unit 130 constant and change the amount of the force applied to the target surface 115 at regular intervals.

According to an embodiment, with the footprint generator 100 capable of applying a constant certain force and the footprint generation method 200 using the footprint generator 100, a user may generate a footprint by applying a certain amount of force.

Therefore, according to an embodiment, footprints may be generated by applying various levels of force to the suspect's shoes when determining whether they are identical with the footprints at the crime scene, or by applying a constant force repeatedly to control variables during a footprint experiment.

As such, according to an embodiment, it can be expected to effectively solve criminal cases by enhancing the reliability of footprint analysis technology.

According to embodiments, when a shoe mounting member on which a shoe is mounted is brought into contact with a target surface, a footprint may be generated by applying a constant force desired by a user to the target surface.

In the embodiments, not only may footprints be generated by repeatedly applying a constant force to a target surface, but also various levels of force may be applied in various ways, thereby enhancing the reliability of footprint analysis technology.

It should be understood that embodiments described herein should be considered in a descriptive sense only and not for purposes of limitation. Descriptions of features or aspects within each embodiment should typically be considered as available for other similar features or aspects in other embodiments. Therefore, the scope of the disclosure is defined by the appended claims.

What is claimed is:

1. A footprint generator capable of applying a constant force, the footprint generator comprising:
    a base plate in which a target surface is on an upper surface of the base plate;
    a shoe mounting member that is apart from the upper surface of the base plate and capable of mounting a shoe;
    a driving unit that is apart from the upper surface of the base plate and capable of moving the shoe mounting member up and down;
    a fixing unit configured to be directly connected to the base plate and fix the shoe mounting member and the driving unit in a position apart from the upper surface of the base plate;
    a force measuring unit configured to measure an impact force when the shoe mounting member descends and contacts the shoe with the target surface to generate a footprint on the target surface;
    an input unit configured to receive an input signal according to a user input;
    a control unit configured to operate the driving unit according to the user input to control the shoe mounting member on which the shoe is mounted to descend and generate the footprint on the target surface by an impact; and
    a display unit configured to display user input information capable of operating the driving unit with a constant force or operation information of the driving unit,
    wherein the driving unit is formed in a shape rotatable about a horizontal axis, and is capable of rotating the shoe mounting member at a certain angle or more about the horizontal axis of the driving unit,
    wherein the shoe mounting member comprises: a shoe fixing unit capable of fixing the shoe and adjustable based on length of the shoe; and a connecting unit formed to connect the driving unit to the shoe fixing unit to rotate the shoe fixing unit about the horizontal axis of the driving unit, and wherein the user input information comprises: the amount of force applied to the target surface, number of times the driving unit is operated, or an angle at which the shoe mounting member rotates about the horizontal axis of the driving unit.

2. The footprint generator capable of applying a constant force of claim 1, wherein the input unit, the control unit, and the display unit are formed as a single control panel.

3. A footprint generation method using a footprint generator capable of applying a constant force, the footprint generation method comprising:

mounting a shoe on a shoe mounting member of the footprint generator including a base plate, the shoe mounting member, a driving unit, and a force measuring unit;

applying a colored solution to a sole of the shoe; and generating a footprint on the target surface by lowering the shoe mounting member to contact the shoe with a target surface located on an upper surface of the base plate.

4. A footprint generation method using a footprint generator capable of applying a constant force, the footprint generation method comprising:

mounting a shoe on a shoe mounting member of the footprint generator including a base plate, the shoe mounting member, a driving unit, and a force measuring unit; and generating a footprint on the target surface by lowering the shoe mounting member to contact the shoe with a target surface located on an upper surface of the base plate, wherein the footprint generator further comprises an input unit, a control unit, and a display unit, and the footprint generation method further comprises:

obtaining user input information capable of operating the driving unit with a constant force after the mounting of a shoe on the shoe mounting member.

5. The footprint generation method using a footprint generator capable of applying a constant force of claim 3, wherein the generating of a footprint on the target surface comprises:

generating a plurality of footprints by applying a constant force to the target surface or generating a footprint while changing the amount of force applied to the target surface at certain intervals, based on the obtained user input information.

6. The footprint generation method using a footprint generator capable of applying a constant force of claim 4, wherein the generating of a footprint on the target surface comprises:

generating a plurality of footprints by applying a constant force to the target surface or generating a footprint while changing the amount of force applied to the target surface at certain intervals, based on the obtained user input information.

* * * * *